(12) United States Patent
Liu

(10) Patent No.: US 8,475,825 B2
(45) Date of Patent: Jul. 2, 2013

(54) CYANOACRYLATE INITIATOR SYSTEM

(75) Inventor: Hongbo Liu, Hillsborough, NJ (US)

(73) Assignee: Ethicon, Inc., Somerville, NJ (US)

( * ) Notice: Subject to any disclaimer, the term of this patent is extended or adjusted under 35 U.S.C. 154(b) by 368 days.

(21) Appl. No.: 12/786,896

(22) Filed: May 25, 2010

(65) Prior Publication Data
US 2010/0330027 A1    Dec. 30, 2010

Related U.S. Application Data

(60) Provisional application No. 61/221,724, filed on Jun. 30, 2009.

(51) Int. Cl.
*A61F 2/00* (2006.01)

(52) U.S. Cl.
USPC .................................................. 424/423

(58) Field of Classification Search
None
See application file for complete search history.

(56) References Cited

U.S. PATENT DOCUMENTS

| | | | |
|---|---|---|---|
| 2,721,858 A | 10/1955 | Joyner et al. | |
| 3,254,111 A | 5/1966 | Hawkins et al. | |
| 3,903,055 A * | 9/1975 | Buck | 526/194 |
| 3,940,362 A | 2/1976 | Overhults | |
| 3,995,641 A | 12/1976 | Kronenthal et al. | |
| 4,291,131 A | 9/1981 | McIntire et al. | |
| 4,313,865 A | 2/1982 | Teramoto et al. | |
| 4,364,876 A | 12/1982 | Kimura et al. | |
| 4,560,723 A | 12/1985 | Millet et al. | |
| 4,720,513 A | 1/1988 | Kameyama et al. | |
| 5,328,687 A | 7/1994 | Leung et al. | |
| 5,514,371 A | 5/1996 | Leung et al. | |
| 5,514,372 A | 5/1996 | Leung et al. | |
| 5,525,647 A * | 6/1996 | Eichmiller | 523/105 |
| 5,575,997 A | 11/1996 | Leung et al. | |
| 5,582,834 A | 12/1996 | Leung et al. | |
| 5,624,669 A | 4/1997 | Leung et al. | |
| 5,928,611 A | 7/1999 | Leung | |
| 5,982,621 A | 11/1999 | Li | |
| 6,143,352 A | 11/2000 | Clark et al. | |
| 6,183,593 B1 | 2/2001 | Narang et al. | |
| 6,310,166 B1 | 10/2001 | Hickey et al. | |
| 6,352,704 B1 | 3/2002 | Nicholson et al. | |
| 6,512,023 B1 | 1/2003 | Malofsky et al. | |
| 6,579,469 B1 | 6/2003 | Nicholson et al. | |
| 6,595,940 B1 | 7/2003 | D'Alessio et al. | |
| 6,743,858 B2 | 6/2004 | Hickey et al. | |
| 7,238,828 B2 | 7/2007 | Liu | |
| 7,534,907 B2 | 5/2009 | Liu | |
| 2003/0039781 A1 | 2/2003 | D'Alessio et al. | |
| 2003/0077386 A1 * | 4/2003 | Azevedo | 427/207.1 |

(Continued)

*Primary Examiner* — James H Alstrum Acevedo
*Assistant Examiner* — Thor Nielsen

(57) ABSTRACT

The present invention is directed to curable compositions that comprise a non-porous substrate, one or more cyanoacrylate polymerization initiators and a prepolymer composition comprising at least one liquid cyanoacrylate monomer or mixture of such monomers (solid or liquid) and/or cyanoacrylate oligomers. The non-porous substrate is a collection of individual particulates that are not bound, bonded or fixed to one another. At least one initiator is deposited on the surface of the individual particulates to form a plurality of initiator carriers. The prepolymer composition receives the plurality of initiator carriers to begin a controlled and consistent polymerization or curing of the liquid cyanoacrylate monomer in order to produce a biocompatible adhesive composition for use on living tissue. The present invention also provides for methods of making and using and devices for such a curable compositions, particularly in treating living tissue by applying to living tissue a biocompatible adhesive composition.

7 Claims, 2 Drawing Sheets

U.S. PATENT DOCUMENTS

| | | |
|---|---|---|
| 2005/0147457 A1 | 7/2005 | Badejo et al. |
| 2005/0196431 A1 | 9/2005 | Narang et al. |
| 2007/0213553 A1 | 9/2007 | Liu et al. |
| 2010/0030258 A1 | 2/2010 | Badejo et al. |

* cited by examiner

CYANOACRYLATE INITIATOR SYSTEM

This application is a Non-Provisional claiming priority from U.S. Provisional Application No. 61/221724, which was filed on Jun. 30, 2009. The complete disclosures of the aforementioned related U.S. patent applications are hereby incorporated herein by reference for all purposes.

BACKGROUND OF THE INVENTION

1. Field of Invention

The present invention relates to a composition used for controlled polymerization of 2-cyanoacrylate monomers and derivatives thereof, particularly, this invention relates to initiator or initiators disposed onto the surface of non-porous substrate for controlled and consistent polymerization of 2-cyanoacrylate monomers and derivatives thereof.

2. Description of Related Art

Monomer and polymer adhesives are used in both industrial (including household) and medical applications. Included among these adhesives are the 1,1-disubstituted ethylene monomers and polymers, such as the α-cyanoacrylates. Since the discovery of the adhesive properties of such monomers and polymers, they have found wide use due to the speed with which they cure, the strength of the resulting bond formed, and their relative ease of use. These characteristics have made the α-cyanoacrylate adhesives the primary choice for numerous applications such as bonding plastics, rubbers, glass, metals, wood, and, more recently, biological tissues.

It is known that monomeric forms of α-cyanoacrylates are extremely reactive, polymerizing rapidly in the presence of even minute amounts of an initiator, including moisture present in the air or on moist surfaces such as animal (including human) tissue. Monomers of α-cyanoacrylates are anionically polymerizable or free radical polymerizable or polymerizable by zwitterions or ion pairs to form polymers. Once polymerization has been initiated, the cure rate can be very rapid.

Medical applications of 1,1-disubstituted ethylene adhesive compositions include use as an alternate or an adjunct to surgical sutures and/or staples in wound closure, as well as for covering and protecting surface wounds such as lacerations, abrasions, burns, stomatitis, sores, minor cuts and scrapes, and other wounds. When an adhesive is applied to surfaces to be joined, it is usually applied in its monomeric form, and the resultant polymerization gives rise to the desired adhesive bond.

U.S. Pat. No. 5,928,611 discloses an applicator tip having a polymerization or cross-linking initiator or accelerator disposed on or in a solid support in the applicator tip. The patent also generally discloses that the initiator may be incorporated into the applicator during the fabrication of the tip, such as by mixing the initiator with the applicator material prior to molding the applicator tip material into the desired form. However, the specifics of and problems associated with this process are not set forth. The patent also discloses suitable initiators as including, for example, benzyltributylammounium bromide and benzylhexadecylammonium chloride.

U.S. Pat. No. 5,982,621 discloses biocompatible cyanoacrylate adhesive compositions that include a monomer, plasticizing agent, an acidic stabilizing agent and an initiator. The initiator may be applied to the surface of the applicator tip or may be impregnated or incorporated into the matrix or internal portions of the applicator tip. However, the specifics of and problems associated with this process are not set forth. The patent also discloses suitable initiators as including, for example, tetrabutyl ammonium bromide and amines.

U.S. Pat. No. 5,525,647 discloses a method and a device for controllably affecting the reaction of dental adhesive. The device comprises an instrument or mixing container that has the reaction affecting compound deposited and affixed into or onto the surface thereof. The reaction affecting compound may be selected from the group consisting of a catalyst, a stabilizer, an antioxidant and an initiator. The instrument or mixing container may be selected from a bristle brush, sponge, absorptive pledget, or mixing well. Preferred co-initiators disclosed in the reference are secondary amines, aliphatic amines, or tertiary amines.

U.S. Pat. No. 4,291,131 discloses a nozzle for use on containers for holding cyanoacrylate adhesives, the nozzle being comprised of moldable material having an organic acid dispersed therein for inhibiting the polymerization of the adhesive within the nozzle. Suitable moldable materials include polyethylene, polypropylene, and crystallizable copolymers of polyethylene and polypropylene. Suitable acids include citric acid, tartaric acid, maleic acid and fumaric acid.

U.S. Pat. Nos. 5,514,371, 5,514,372, 5,575,997, 5,624,669, and 5,582,834 disclose cyanoacrylate compositions, and suitable initiators for initiating polymerization of the cyanoacrylate compositions.

U.S. Pat. No. 3,903,055 discloses a method of using porous particulates such as molecular sieves as initiator carrier to achieve predetermined and reproducible gel/transition times for small amount of cyanoacrylate adhesives. The use of porous substrates as initiator carriers may introduce inherent variability in loading of the initiator and subsequent extraction of the initiator by the adhesives from the carrier due to non-uniform porosity of the carrier. In the event where the initiator is deposited into pores too small in size, the initiator may not be in contact with the adhesives thus not utilized, so it is difficult to control the adhesive cure time based on the amount of initiator loaded on the porous carrier.

Published US Patent Application No. 2005/0147457 discloses adhesive compositions and adhesive applicators, particularly suitable for cyanoacrylate adhesives, with polymerization initiators and rate modifiers.

SUMMARY OF THE INVENTION

The present invention is directed to curable compositions that comprise a non-porous substrate, one or more cyanoacrylate polymerization initiators and a prepolymer composition comprising at least one liquid cyanoacrylate monomer or mixture of such monomers (solid or liquid) and/or cyanoacrylate oligomers. The non-porous substrate is in particulate form as a collection of individual particulates that are not bound, bonded or fixed to one another. The one or more initiators are, with respect to the non-porous substrate, deposited only on the surface of the individual particulates to form a plurality of initiator carriers. The prepolymer composition receives the plurality of initiator carriers to begin a controlled and consistent polymerization or curing of the liquid cyanoacrylate monomer to produce a biocompatible adhesive composition for use on living tissue.

The present invention also provides a method of making such a curable composition comprising: providing one or more polymerization initiators onto the surface of a plurality of non-porous substrates and combining the coated initiator carriers and a prepolymer composition in a system that prevents the components from contacting one another, wherein the non-porous substrates are not bound, bonded or fixed to one another in such system and the prepolymer composition and the initiator carrier are in a non-contacting relationship with one another.

The present invention also provides a method of using a curable composition in treating living tissue by applying to living tissue a biocompatible adhesive composition resulting from the combination of a cyanoacrylate prepolymer composition and a plurality of initiator carriers, each initially contained in a container as separate components. Prior to application to the tissue, the plurality of initiator carriers are allowed to contact and become thoroughly admixed into the prepolymer composition. The resulting polymer or at least partially polymerized material is then separated from the plurality of initiator carriers and dispensed from container onto living tissue.

The present invention also relates to devices that are particularly suitable for storage of initiator carrier and the adhesive prepolymer composition, effective mixing and delivery of the resulting adhesive composition for its intended use, such as a tissue sealant.

DETAILED DESCRIPTION OF PREFERRED EMBODIMENTS

Figure 1:
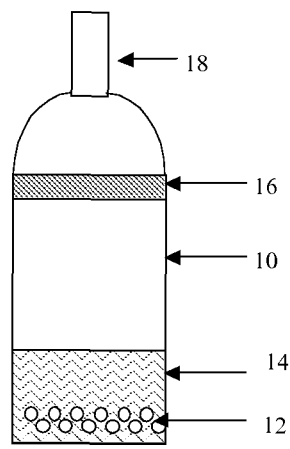
FIG. 1 is a schematic representation of a device suitable for use with the present invention.

The present invention is directed to curable compositions that comprise a non-porous substrate, one or more cyanoacrylate polymerization initiators and a prepolymer composition comprising at least one liquid cyanoacrylate monomer or mixture of such monomers (solid or liquid) and/or cyanoacrylate oligomers. The non-porous substrate is in particulate form as a collection of individual particulates that are not bound, bonded or fixed to one another. The one or more initiators are, with respect to the non-porous substrate, deposited only on the surface of the individual particulates to form a plurality of initiator carriers. The prepolymer composition receives the plurality of initiator carriers to begin a controlled and consistent polymerization or curing of the liquid cyanoacrylate monomer.

According to the present invention, the non-porous substrate should be substantially uniform in size and coated with an initiator to form initiator carriers. "Uniformity" as used herein refers to size distribution of the non-porous particulates having the ratio of upper size to lower size that is less than about 2, more preferably less than or equal to 1.5.

The particulates prior to being coated with initiator can be characterized by either their particle size or mesh size; these two parameters can be readily converted mathematically by known methods in the field. The particulates preferably have average particle size from about 0.05 mm to about 5 mm. More preferred average particles size ranges from about 0.10 mm to about 2.5 mm, even more preferred from about 0.15 mm to about 2.5 mm. Alternatively, if characterized by mesh size, particulates can have a mesh size from about 3 to about 270 US mesh with preferred mesh size ranging from about 7 to about 140 US mesh and more preferred mesh size ranging from about 7 to about 100 US mesh.

Alternatively, the particulates can be characterized by their specific surface area (SSA, in units of $m^2/g$ or $cm^2/g$) wherein SSA is defined as the ratio of the absolute surface area of a solid to its mass. Methods to determine the SSA of a solid are readily known, such as Brunauer, Emmett and Teller (BET) method. Use of specific surface area (SSA) to characterize the particulates in this invention may be particularly useful in estimating initiator loading capacity of the carriers because the initiator is loaded onto the surface of the non-porous particulates. For example, if the particulates are made from glass, the plurality of carriers should have an average specific surface area from about 20 to about 1000 $cm^2/g$. Preferred specific surface area is from about 30 to about 850 $cm^2/g$. More preferred specific surface area is from 30 to 600 $cm^2/g$.

The non-porous particulates described in this invention can be made from any materials that are solid at room temperature. These materials can be inorganic, organic or inorganic-organic hybrid in nature. Suitable organic materials include polymers and oligomers. Inorganic materials include glass, ceramics, or metallic materials. Materials particularly useful as non-porous particulates do not form covalent bonding with the initiators deposited thereon. In addition, the carrier materials should not interact or react with the adhesive prepolymer described below to cause/initiate substantial premature polymerization. Examples of particularly suitable materials are inorganic or metallic materials, including, without limitation, glass, ceramics, and metallic materials. Glass or ceramic materials are the most preferred materials for use as the non-porous particulate.

According to this invention, one or more initiators can be applied to the non-porous particulate by processes generally known in the art, such as solution coating, spraying, dipping, brushing and vapor deposition. With the exception of vapor deposition, the initiator(s) can be applied to the surface of the non-porous substrate with a liquid medium containing the initiator in a liquid carrier at room temperature or as molten liquid at an elevated temperature or pressure. The liquid medium can be either aqueous or organic in nature, such as, ethanol, methanol, acetonitrile, DMSO, DMF, ethylacetate, ether, acetone, pentane, or mixtures thereof. Preferably, the liquid medium is a solvent that can be easily removed, for example, by evaporation. Alternatively, the initiator may be applied onto the carrier material by vapor deposition without the use of solvents. The selection of a suitable carrier material may depend on the process used to deposit the polymerization initiators. For example, an organic material, such as a polymer material that swells in a selected initiator solution would not be suitable as a carrier material for solution coating process but can be a suitable carrier for the vapor deposition process.

Particular initiators for particular adhesive composition systems may be readily selected by one of ordinary skill in the art without undue experimentation. Suitable initiators include, but are not limited to, detergent compositions; surfactants: e.g., nonionic surfactants such as Polysorbate 20 (e.g., Tween20® surfactant), Polysorbate 80 surfactant (e.g., Tween80® surfactant) and poloxamers, cationic surfactants such as tetra-butyl ammonium bromide and tetra-butyl ammonium chloride, anionic surfactants such as sodium tetradecyl sulfate, and amphoteric or zwitterionic surfactants such as dodecyldimethyl(3-sulfopropyl) ammonium hydroxide, inner salt; amines, imines and amides, such as imidazole, tryptamine, urea, arginine and povidine; phosphines, phosphites and phosphonium salts, such as triphenylphosphine and triethyl phosphite; alcohols such as ethylene glycol, methyl gallate, ascorbic acid, tannins and tannic acid; inorganic bases and salts, such as sodium bisulfite, magnesium hydroxide, calcium sulfate and sodium silicate; sulfur compounds such as thiourea and polysulfides; polymeric cyclic ethers such as monensin, nonactin, crown ethers, calixarenes and polymeric epoxides; cyclic and acyclic carbonates, such as diethyl carbonate; phase transfer catalysts such as Aliquat 336; organometallics such as cobalt naphthenate and manganese acetylacetonate; and radical initiators and radicals, such as di-t-butyl peroxide and azobisisobutyronitrile.

The polymerizable and/or cross-linkable material may also contain an initiator which is inactive until activated by a catalyst or accelerator (included within the scope of the term "initiator" as used herein) on the initiator carriers. Initiators activated by stimulation such as heat and/or light (e.g., ultraviolet or visible light) are also suitable if the container is appropriately subjected to such stimulation.

According to embodiments of the present invention, particularly suitable classes of initiators are quaternary ammonium salts, tertiary amines, and other strong anion exchange resins. Suitable quaternary ammonium salts include, but are not limited to, tetraalkylammonium halides where the alkyl chain is from about 1 to about 20 carbon atoms, such as tetrabutylammonium bromide and tetrabutylammonium chloride; ether amine quaternaries; quaternary ammonium sulfate salts; quaternary ammonium bisulfate salts; benzalkonium chloride; and the like.

In general, quaternary ammonium salts can be represented by the following formulas:

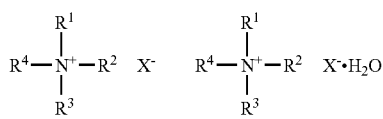

where $X^-$ can be selected from, for example, $Cl^-$, $F^-$, $Br^-$, $I^-$, $SO_4^-$, $HSO_4^-$, $OH^-$, and the like; and $R^1$, $R^2$, $R^3$, and $R^4$ can be the same or different and can be selected from, for example, alkyl groups, aryl groups, aralkyl groups, and the like having from 1 to about 20 carbon atoms. As shown in the above formulas the quaternary ammonium salts can include water of hydration and/or crystallization.

Examples of suitable ether amine quaternaries include, but are not limited to, compounds of the following formula (I):

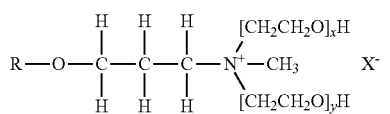

where R is a straight or branched alkyl group of from about 2 to about 20 carbon atoms, preferably from about 4 to about 16 carbon atoms; x and y represent the number of repeating units and independently are integers of from 1 to about 10, preferably from 1 to about 3, 4, or 5; and X is a counterion selected from, for example, halides such as chloride, bromide, iodide, and fluoride, sulfate, hydrogen sulfate, sulfite, hydrogen sulfite, bisulfate, bisulfite, hydroxide, and the like. Suitable examples of such ether amine quaternaries of formula (I) include, but are not limited to, the products Q-14-2 and Q-14-2 PG (isodecyloxypropyl dihydroxyethylmethyl ammonium chloride, where R is branched $C_{10}H_{21}$, X is chloride and x and y yield a molecular weight of about 370), Q-17-2 and Q-17-2 PG (isotridecyloxypropyl dihydroxyethylmethyl ammonium chloride, where R is branched $C_{13}H_{27}$, X is chloride and x and y yield a molecular weight of about 410), and Q-17-5 (isotridecyloxypropyl poly(5) oxyethylene methyl ammonium chloride, where R is branched $C_{13}H_{27}$, X is chloride and x and y yield a molecular weight of about 535), all available from the Tomah3 company. Suitable polymeric tertiary amines include, but are not limited to, the DOWEX® materials available from Dow Chemicals, and the like. Suitable strong anion exchange resins include, but are not limited to, the Amberlyst® materials, available from Rohm & Haas, particularly Amberlyst® A-26, and the like.

Particularly preferred among the quaternary ammonium salts are quaternary ammonium sulfate salts and quaternary ammonium bisulfate salts, such as quaternary ammonium hydrogen sulfates and quaternary ammonium hydrogen bisulfates. Examples of such compounds include, but are not limited to, tetrabutyl ammonium sulfate, tetrabutyl ammonium bisulfate, tetrabutyl ammonium hydrogen sulfate, tetrabutyl ammonium hydrogen bisulfate, tetrabutyl ammonium carbonate, tetrabutyl ammonium bicarbonate, tetrabutyl ammonium sulfite, tetrabutyl ammonium bisulfite, and the like.

Also particularly preferred among the quaternary ammonium salts are such salts that are soluble in the monomer used in the adhesive composition. Thus, for example, particularly preferred are ether amine quaternaries, such as the ether amine quaternaries of formula (I) above. A particular advantage of the quaternary ammonium salts that exhibit increased solubility in the monomer is the ability of the quaternary ammonium salts to more quickly initiate polymerization of the monomer. Thus, for example, a quaternary ammonium salt such as the ether amine quaternaries that is more soluble in the monomer, as compared to benzalkonium chloride, which is less soluble in the monomer, will more quickly and homogeneously initiate polymerization of the monomer. This difference indicates that the tetrabutyl ammonium salts such as tetrabutyl ammonium chloride dissolves into the polymerizable monomer better than benzalkonium chloride. This in turn enables faster setting of the monomer. In addition, in embodiments where multiple layering of the adhesive composition may be desired, the faster setting more easily permit multiple layering of the adhesive composition.

Other initiators include combination of tertiary amines and quaternary ammonium salts being blended or having the dual functional groups in a single compounds, such initiators are disclosed in U.S. patent application Ser. No. 12/183,295, filed on Jul. 31, 2008, and published U.S. patent application Ser. No. 12/415,303 filed Mar. 31, 2009, which are hereby incorporated in their entirety by reference herein.

The amount of initiator used in the present invention will generally depend upon the desired monomer and desired initiator being used, the type of initiator carrier being used, and other process conditions. However, generally, the amount of initiator can vary from about 0.0001% to as high as 50% by weight of the polymerizable monomer composition. Preferably, in embodiments, the initiator is present in an amount of from 0.001% to 25%, and more preferably from 0.01% to 10% by weight.

The monomer (including prepolymeric) adhesive composition may include one or more polymerizable monomers. Preferred monomers that may be used in this invention are readily polymerizable, e.g. anionically polymerizable or free radical polymerizable or polymerizable by zwitterions or ion pairs to form polymers. Such monomers include those that form polymers, that may, but do not need to, biodegrade. Such monomers are disclosed in, for example, U.S. Pat. Nos. 5,328, 687, 5,928,611, 6,183,593, 7,534,907 and 7,238,828, which are hereby incorporated in their entirety by reference herein. Preferred monomers include 1,1-disubstituted ethylene monomers, such as α-cyanoacrylates including, but not limited to, alkyl α-cyanoacrylates having an alkyl chain length of from about 1 to about 20 carbon atoms or more, preferably from about 3 to about 8 carbon atoms.

The α-cyanoacrylates of the present invention can be prepared according to several methods known in the art. U.S. Pat. Nos. 2,721,858, 3,254,111, 3,995,641, 4,364,876, and published U.S. Patent Application No. 2007/0213553, each of which is hereby incorporated in their entirety by reference herein, disclose methods for preparing α-cyanoacrylates.

The composition may optionally also include at least one other plasticizing agent that assists in imparting flexibility to the polymer formed from the monomer. The plasticizing agent preferably contains little or no moisture and should not significantly affect the stability or polymerization of the monomer. Examples of suitable plasticizers include but are not limited to acetal trihexyl citrate, cetyl trihexyl citrate, fatty acid esters, tributyl citrate, acetyl tri-n-butyl citrate (ATBC), polymethylmethacrylate, polydimethylsiloxane, hexadimethylsilazane and others as listed in U.S. Pat. No. 6,183,593, the disclosure of which is incorporated in its entirety by reference herein.

The composition may also optionally include at least one thixotropic agent. Suitable thixotropic agents are known to the skilled artisan and include, but are not limited to, silica gels such as those treated with a silyl isocyanate, and optionally surface treated titanium dioxide. Examples of suitable thixotropic agents and thickeners are disclosed in, for example, U.S. Pat. No. 4,720,513, and U.S. Pat. No. 6,310,166, the disclosures of which are hereby incorporated in their entireties by reference herein. The composition may optionally also include thickeners. Suitable thickeners may include preformed polymers of cyanoacrylates, polymethylmethacrylate, poly (lactic acid), poly (glycolic acid), polycaprolactone and copolymers as disclosed in U.S. Pat. No. 6,743,858, the disclosure of which is incorporated by reference herein in its entirety.

The composition may also optionally include at least one natural or synthetic rubber to impart impact resistance. Suitable rubbers are known to the skilled artisan. Such rubbers include, but are not limited to, dienes, styrenes, acrylonitriles, and mixtures thereof. Examples of suitable rubbers are disclosed in, for example, U.S. Pat. Nos. 4,313,865 and 4,560,723, the disclosures of which are hereby incorporated in their entireties by reference herein.

The composition may optionally also include one or more stabilizers, preferably both at least one anionic vapor phase stabilizer and at least one anionic liquid phase stabilizer. These stabilizing agents may inhibit premature polymerization. Suitable stabilizers may include those listed in U.S. Pat. No. 6,183,593, the disclosure of which is incorporated by reference herein in its entirety. Furthermore, certain stabilizers may also function as anti-fungal agents, such as, for example, various acidic anti-fungals, as identified above. Other stabilizing agents, such as various free radical stabilizing agents, can also be used alone or in combination with the above stabilizers. Suitable free radical stabilizing agents are disclosed in, for example, U.S. Pat. No. 6,512,023, the entire disclosure of which is incorporated by reference herein.

The stability, and thus the shelf-life, of some monomeric adhesive compositions can be further enhanced and extended through careful regulation of the packaging. Treated (e.g., fluorinated polymer) packaging s is preferred and may reduce the amount of stabilizer that is combined into the composition. As mentioned above, certain stabilizers including, but not limited to, certain acidics can also function as anti-fungal agents. In this case, the amount of the anti-fungal/stabilizer material is either not reduced below a level to provide the desired anti-fungal effect, or a further anti-fungal/non-stabilizing agent is added to ensure that the desired anti-fungal effect is provided.

The compositions may also include pH modifiers to control the rate of degradation of the resulting polymer, as disclosed in U.S. Pat. No. 6,143,352, the entire disclosure of which is hereby incorporated by reference herein in its entirety.

Compositions of the present invention may also include at least one biocompatible agent effective to reduce active formaldehyde concentration levels produced during in vivo biodegradation of the polymer (also referred to herein as "formaldehyde concentration reducing agents"). Preferably, this component is a formaldehyde scavenger compound. Examples of formaldehyde scavenger compounds useful in this invention include sulfites; bisulfites; mixtures of sulfites and bisulfites, etc. Additional examples of formaldehyde scavenger compounds useful in this invention and methods for their implementation can be found in U.S. Pat. Nos. 5,328,687, 5,514,371, 5,514,372, 5,575,997, 5,582,834 and 5,624,669, which are hereby incorporated herein by reference in their entireties.

To improve the cohesive strength of adhesives formed from the compositions of this invention, difunctional monomeric cross-linking agents may be added to the monomer compositions of this invention. Such crosslinking agents are known. U.S. Pat. No. 3,940,362, which is hereby incorporated herein in its entirety by reference, discloses exemplary cross-linking agents.

The compositions of this invention may further contain fibrous reinforcement and colorants such as dyes, pigments, and pigment dyes. Examples of suitable fibrous reinforcement include PGA microfibrils, collagen microfibrils, and others as described in U.S. Pat. No. 6,183,593, (the disclosure of which is incorporated by reference herein in its entirety.

The polymerizable compositions useful in the present invention may also further contain one or more preservatives, for prolonging the storage life of the composition. Suitable preservatives, and methods for selecting them and incorporating them into adhesive compositions, are disclosed in U.S. Pat. No. 6,579,469, the entire disclosure of which is incorporated herein by reference. Such preservatives can be in addition to any anti-fungal agent that may or may not be added to the composition, as described above.

In embodiments, the monomer composition and/or its packaging are preferably sterilized. Sterilization of the monomer composition and/or its packaging can be accomplished by techniques known to one of ordinary skill in the art, and is preferably accomplished by methods including, but not limited to, chemical, physical, and/or irradiation methods. Examples of chemical methods include, but are not limited to, exposure to ethylene oxide or hydrogen peroxide vapor. Examples of physical methods include, but are not limited to, sterilization by heat (dry or moist) or retort canning. Examples of irradiation methods include, but are not limited to, gamma irradiation, electron beam irradiation, and microwave irradiation. The composition must show low levels of toxicity to living tissue during its useful life. In preferred embodiments of the present invention, the composition is sterilized to provide a Sterility Assurance Level (SAL) of at least $10^{-3}$. In embodiments, the Sterility Assurance Level may be at least $10^{-4}$, or may be at least $10^{-5}$, or may be at least $10^{-6}$.

Suitable materials and applicators and packaging systems are disclosed in U.S. Pat. Nos. 5,928,611, 6,579,469, 6,352,704 and 6,595,940, published US Patent application No.

2005/0196431, and published US Patent application No. 2003/0039781; the entire disclosures of which are incorporated herein by reference.

Glass beads will be used in further illustrating the invention. Briefly, in carrying out the polymerization method of this invention, a quantity of prepolymer is measured into a suitable container and a plurality of initiator carriers is introduced. The mixture is agitated to allow time for dissolution and diffusion of an adequate quantity of initiator from the glass beads into the prepolymer. After a measured time, the initiator carriers are separated from the monomer, for example, by the action of a filtering device to allow the monomer applied without the initiator carrier for intended application.

Prepolymer cure rate can be regulated by controlling the quantity of initiator carriers used, initiator loading on the particulates and/or the selection of the initiators. In general, the greater the amounts of initiator present in the prepolymer the faster the cure rate.

This invention also relates to suitable devices appropriate for achieving effective initiation of adhesive prepolymer and expression of the initiated prepolymer for intended applications with controlled cure time. Such a device may comprise members include, a) a container where the adhesive prepolymer is placed into; b) optionally, a separate container for the placement of initiator carrier; c) a mechanism for the introduction of initiator carrier to be in contact with the adhesive prepolymer; d) a container where the initiator carrier and the adhesive prepolymer can be effectively mixed to allow sufficient dissolution and distribution of initiator from the carrier into the adhesive prepolymer; e) optionally, a mechanism by which the initiated adhesive prepolymer is separated from the initiator carrier after mixing; f) a mechanism by which the initiated prepolymer can be expressed and applied for intended application; g) optionally, a mechanism by which the initiated adhesive prepolymer can be applied in a desired fashion.

Figure 2:
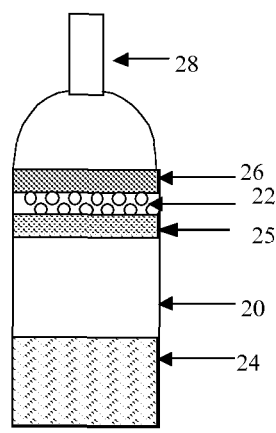
FIG. 2 is a schematic representation of a device suitable for use with the present invention.
Figure 3:
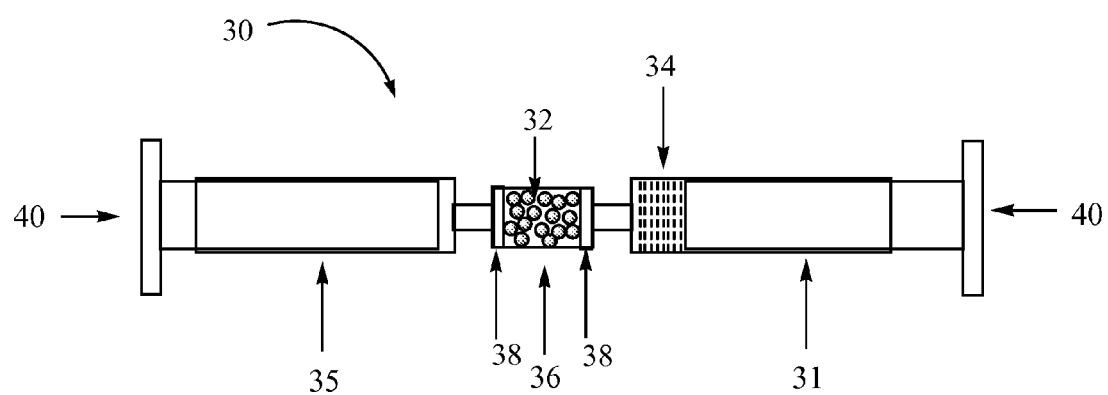
FIG. 3 is a schematic representation of a device suitable for use with the present invention.

Examples of such suitable devices are given in FIGS. 1, 2, and 3. However, suitable devices performing same functions are not limited by these examples. In FIG. 1, a plurality of initiator carriers 12 is directly introduced into an adhesive prepolymer material 14 in container 10. The dissolution and distribution of the initiator from the plurality of carriers 12 into the adhesive prepolymer material 14 can be achieved by suitable means of agitation such as shaking, vortexing and ultrasonication, etc. The initiated adhesive prepolymer material 14 is then expressed through filter 16 to separate the now initiated adhesive prepolymer material 14 from the plurality of initiator carriers 12. A suitable tip 18 can be used so the initiated adhesive prepolymer can be applied in a desired fashion. Suitable tip designs include those capable of applying the initiated adhesive prepolymer into a thin film with precise width, a beaded line, or a sprayed layer.

Alternatively, as shown in FIG. 2, the adhesive prepolymer material 24 is separated from the plurality of initiator carriers 22 by a divider 25 within container 20. In use, divider 25 is broken, ruptured, fractured in such a manner as to allow the plurality of initiator carriers 22 to come into contact with the adhesive prepolymer material 24. The dissolution and distribution of the initiator from the plurality of carriers 22 into the adhesive prepolymer material 24 can be achieved by suitable means of agitation such as shaking, vortexing and ultrasound mixing, etc. The initiated adhesive prepolymer material 24 is then expressed through filter 26 to separate the now initiated adhesive prepolymer material 24 from the plurality of initiator carriers 22. A suitable tip 28 can be used so the initiated adhesive prepolymer material 24 can be applied in a desired fashion. Suitable tip designs include those capable of applying the initiated adhesive prepolymer into a thin film with precise width, a beaded line, or a sprayed layer.

Alternatively, as shown in FIG. 3, a dual-syringe type device 30 can be used. Adhesive prepolymer material 34 is placed into a first syringe 31, while a plurality of initiator carriers 32 are confined to a coupled container 36. Second syringe 35 is attached, preferably in a releasable fashion, to coupled container 36. First syringe 31, coupled container 36, and second syringe are all in fluid communication with one another. Filter members 38 are preferably provided on opposing ends of coupled container 36 in order to retain the plurality of initiator carriers 32 therein, To achieve the desired dissolution and distribution of the initiator from the plurality of initiator carriers 32 into the adhesive prepolymer material 34, the adhesive prepolymer material 34 is forced from first syringe 31 through the coupled container 36 and the plurality of initiator carriers 32 in a back-and-forth fashion by the action of syringe plungers 40 provided on each syringe. Once the adhesive prepolymer material 34 has made at least one, typically at least three, passes through the coupled container 36 for the plurality of initiator carriers 32, a sufficient amount of initiator is present in the adhesive prepolymer. Either syringe (31 or 35) containing the initiated adhesive prepolymer is disconnected from the rest of device. A suitable tip (not shown), such as those described in FIG. 1 and FIG. 2, can be attached to the separated syringe (31 or 35) for the application of the now initiated adhesive prepolymer material 34.

Suitable devices performing similar functions of this invention may vary in shape and form and can be designed by those skilled in the art. For example, a secondary container can be used to contain the adhesive prepolymer, rather than the plurality of initiator carries inside the described container (FIG. 2). The adhesive prepolymer is released from this secondary container prior to the introduction of the initiator carrier and/or the mixing between the initiator carrier and the adhesive prepolymer. Suitable secondary container can be made from, but not limited to, glass, plastic, or aluminum materials that can be easily crashed open or punctured to allow the release of the adhesive prepolymer.

The following examples illustrate specific embodiments of the present invention. One skilled in the art will recognize that the appropriate reagents and component ratios/concentrations may be adjusted as necessary to achieve specific product characteristics. All parts and percentages are by weight unless otherwise indicated.

EXAMPLE 1

Preparation of Initiator Stock Solutions 250.0 mg of benzyltributylammounium bromide (BTABr) (Fisher Scientific) is dissolved into 250.0 ml absolute ethanol to produce 1.00 mg/ml primary solution. 25.0 ml of this primary solution is diluted with 225.0 ml absolute ethanol to produce 0.100 mg/ml final solution. Benzylhexadecylammonium chloride (BHC) (Sigma-Aldrich) solutions are prepared using the above procedure.

EXAMPLE 2

Preparation of Initiator Carriers 10.0 g of glass beads (710~1180 micron) are mixed with 50.0 ml of 0.100 mg/ml BTABr ethanol solution in a 250 ml round-bottom flask. The solvent is evaporated using a rotary evaporator. The beads are further dried under vacuum (~1 mmHg) overnight. The loading of the initiator on beads is labeled as 0.500 mg/g. BHC coated beads are prepared using the same procedure.

EXAMPLE 3

Preparation of Initiator Carriers 10.0 g of glass beads (710~1180 micron) are mixed with 25.0 ml of 0.100 mg/ml BTABr ethanol solution in a 250 ml round-bottom flask. Additional 25.0 ml absolute ethanol is added to above mixture. The solvent is evaporated using a rotary evaporator. The beads are further dried under vacuum (~1 mmHg) overnight. The loading of the initiator on beads is labeled as 0.250 mg/g. BHC impregnated beads are prepared using the same procedure.

EXAMPLE 4

Cure Time of Adhesive by Initiator Carriers

The tack-free cure time test is conducted using the following procedure as an example. 0.50 ml of 2-octylcyanoacrylate (2-OCA) is placed in the device. 100.0 mg of initiator carriers (710~1180 micron) coated with BTABr (0.500 mg/g) is added to the device while a stopwatch is activated. The tip cover is quickly placed to close the device chamber. The initiator carriers and adhesive mixture is immediately mixed by vigorous shaking for about 15 seconds to initiate the curing. This activated adhesive is expressed through the flat tip of the device onto a clean glass slides. A total of at least 6 isolated adhesive strips (~0.5 cm×2 cm) are produced on the glass slides. These adhesive strips are individually examined by visual sign of complete cure and by the touch of lab latex glove fingers to determine tackiness. The time to reach tack-free cure is recorded for all samples and reported as a range of time from the first to cure to the last to cure. Porous silica gel (Sigma-Aldrich) coated with BTABr (1.00 mg/g) is also tested.

The results are summarized in Table 1.

EXAMPLE 5

Cure Time of Adhesive by Initiator Carriers

The tack-free cure time was conducted using the following procedure as an example.

Calculated amount of initiator carriers with desired amount of initiator loading was placed in a glass vial equipped with a magnetic stir bar. Calculated amount of adhesive, 3-(2-Cyano-acryloyloxy)-hexanoic acid ethyl ester (Et-b-CPL-CA), is added to this glass vial while the mixture is stirred using a magnetic stirrer at ~600 rpm for 30 seconds. A stopwatch is started at the beginning of the mixing. The adhesive is immediately transferred into a lab prototype device as shown in Example 4. After placing the tip cover, the adhesive was applied to clean glass slides through the flat tip into at least 6 isolated adhesive strips of ~0.5 cm×2 cm each. Tack-free cure time of these adhesive strips is recorded as described in Example 4. The results are summarized in Table 2.

TABLE 2

Cure time of Et-b-CPL-CA by initiator carriers

| | Initiator Carriers | | | Adhesive | |
|---|---|---|---|---|---|
| Initiator | Size (micron) | Initiator Loading (mg/g) | Weight (mg) | Et-b-CPL-CA (ml) | Cure time |
| BTABr | 710~1180 | 0.250 | 200.0 | 0.50 | ~20 min |
| | 710~1180 | 0.500 | 150.0 | 0.50 | 3 min~ 3 min 30 s |
| | 710~1180 | 0.500 | 200.0 | 0.50 | 30 s |

EXAMPLE 6

A sample of an adhesive sample having an initiator impregnated porous plug is used to perform the following test.

The initiator impregnated porous plug is fitted into an appropriate housing unit. This unit is attached to another

TABLE 1

Cure time of 2-OCA by initiator carriers

| | Initiator Carriers | | | Adhesive | |
|---|---|---|---|---|---|
| Initiator | Size (micron) | Initiator Loading (mg/g) | Weight (mg) | 2-OCA (ml) | Cure time |
| BTABr | 150~212 | 0.250 | 100.0 | 0.50 | ~15 min |
| | 150~212 | 0.500 | 100.0 | 0.50 | 12 min~13 min |
| | 425~600 | 0.250 | 100.0 | 0.50 | 9 min~10 min |
| | 425~600 | 0.500 | 100.0 | 0.50 | 8 min~9 min |
| | 710~1180 | 0.250 | 100.0 | 0.50 | 7 min 30 s~8 min |
| | 710~1180 | 0.500 | 100.0 | 0.50 | 2 min 30 s~3 min 30 s |
| BHC | 150~212 | 0.250 | 100.0 | 0.50 | >15 min |
| | 150~212 | 0.500 | 100.0 | 0.50 | >15 min |
| | 425~600 | 0.250 | 100.0 | 0.50 | 8 min~9 min 30 s |
| | 425~600 | 0.500 | 100.0 | 0.50 | 6 min~7 min 30 s |
| | 710~1180 | 0.250 | 100.0 | 0.50 | 6 min 30 s~7 min |
| | 710~1180 | 0.500 | 100.0 | 0.50 | 4 min~4 min 30 s |
| None | 150~212 | None | 100.0 | 0.50 | Not cured up to 25 min |
| | 425~600 | None | 100.0 | 0.50 | Not cured up to 25 min |
| BTABr | Porous Silica Gel Resin 35~60 mesh (250~500 micron, 60 Å) | 1.00 mg/g | 100.0 | 0.50 | Not cured up to 25 min | flexible tubular container containing 2-OCA monomer. Manual pressure is applied to the flexible tubular container to force the liquid monomer through the porous plug. The adhesive passing through the porous plug is applied to a clean glass slide to produce six 0.5 cm×2 cm adhesive strips sequentially. A stopwatch is activated at the beginning of producing the first adhesive strip. These adhesive strips are labeled as 1 through 6 in the order of their formation. The cure time of these adhesive strips are determined as described in Example 4. The results are summarized in Table 3.

TABLE 3

Cure time of A Sample of Product

| | Sequence of application | | | | |
|---|---|---|---|---|---|
| 1 | 2 | 3 | 4 | 5 | 6 |
| Cure time 1 min 30 s | 2 min | 4 min | 5 min 30 s | >15 min | >3 h |

TABLE 4

Specific surface area of the Example Glass Beads

| | Glass Beads (micron) | | | | |
|---|---|---|---|---|---|
| 150 | 212 | 425 | 600 | 710 | 1,180 |
| Specific surface area (cm²/g) 570 | 403 | 201 | 143 | 120 | 72 |

TABLE 5

Initiator Loading by SSA

| Beads Size (micron) | SSA (cm²/g) | Initiator Loading by Beads weight (mg/g) | Initiator Loading by Beads SSA (ug/cm²) |
|---|---|---|---|
| 150 | 570 | 0.50 | 0.88 |
| 212 | 403 | 0.50 | 1.24 |
| 425 | 201 | 0.50 | 2.48 |
| 600 | 143 | 0.50 | 3.51 |
| 710 | 120 | 0.50 | 4.15 |
| 1180 | 72 | 0.50 | 6.90 |

SSA: Specific Surface Area

It is clear that the method of using initiator impregnated beads to initiate the curing of adhesives produced very reproducible cure behavior. The difference in cure time between multiple sequential applications (strips) is very small. It is also clear that the cure time can be controlled by varying the initiator loading on the glass beads. It is also noted that the cure time can be modified by using different initiator.

In comparison, the cure time of adhesive contained in an adhesive sample having an initiator impregnated porous plug is highly dependent on the sequence of application. The first 2 adhesive strips cure in a very consistent fashion between 1 min 30 s to 2 min. However, the following strips cure in much slower rate. The 6$^{th}$ adhesive strip, the last available portion of the adhesive, is not completely cured even after 3 hours.

The size of the beads used has an impact on the effectiveness of initiating the curing of glues. The beads with size of 150~212 micron appear not to be as effective as larger ones. In tests with 2-OCA, beads with size of 150~212 micron and 425~600 micron tend to clump together.

Glass beads uncoated with initiator does not initiate the curing of 2-OCA up to 25 min. Porous silica gel resin (used for column chromatography) was coated with BTABr initiator at 1.00 mg/g loading and tested for initiating the curing of 2-OCA. It was ineffective.

While the invention has been described with reference to preferred embodiments, the invention is not limited to the specific examples given, and other embodiments and modifications can be made by those skilled in the art without departing from the spirit and scope of the invention.

I claim:

1. A curable composition comprising
   a. a non-porous substrate,
   b. one or more cyanoacrylate polymerization initiators and
   c. a prepolymer composition comprising at least one liquid cyanoacrylate monomer or mixture of cyanoacrylate monomers and/or cyanoacrylate oligomers,
   wherein the non-porous substrate is composed of a plurality of individual particulates that are not bound, bonded or fixed to one another and are solid, organic polymeric material or solid, inorganic-organic hybrid material,
   wherein the plurality of individual particulates, prior to being coated with initiator, have a specific surface area from 30 to 600 cm²/g, and
   wherein the one or more cyanoacrylate initiators are deposited on the surface of the plurality of individual particulates to form a plurality of initiator carriers.

2. The curable composition according to claim 1 wherein the plurality of individual particulates, prior to being coated with initiator, have an average particle size from about 0.05 mm to about 5 mm.

3. The curable composition according to claim 1 wherein the plurality of individual particulates, prior to being coated with initiator, have an average particle size of from about 0.10 mm to about 2.5 mm.

4. The curable composition according to claim 1 wherein the plurality of individual particulates, prior to being coated with initiator, have an average particle size of from about 0.15 mm to about 2.5 mm.

5. The curable composition according to claim 1 wherein the plurality of individual particulates, prior to being coated with initiator, have an average mesh size from about 3 to about 270 US mesh.

6. The curable composition according to claim 1 wherein the plurality of individual particulates, prior to being coated with initiator, have an average mesh size ranging from about 7 to about 140 US mesh.

7. The curable composition according to claim 1 wherein the plurality of individual particulates, prior to being coated with initiator, have an average mesh size ranging from about 7 to about 100 US mesh.

* * * * *